(12) United States Patent
Leneau

(10) Patent No.: US 7,635,489 B2
(45) Date of Patent: *Dec. 22, 2009

(54) INGESTION OF HYALURONIC ACID FOR IMPROVED JOINT HEALTH

(75) Inventor: Harry Leneau, Jasper, MO (US)

(73) Assignee: Leneau Holdings, LLC, Jasper, MO (US)

( * ) Notice: Subject to any disclaimer, the term of this patent is extended or adjusted under 35 U.S.C. 154(b) by 1090 days.

This patent is subject to a terminal disclaimer.

(21) Appl. No.: 10/629,880

(22) Filed: Jul. 29, 2003

(65) Prior Publication Data

US 2004/0022847 A1 Feb. 5, 2004

Related U.S. Application Data

(63) Continuation-in-part of application No. 09/860,425, filed on May 18, 2001, now Pat. No. 6,607,745.

(51) Int. Cl.
*A61K 31/728* (2006.01)
*A61K 9/48* (2006.01)

(52) U.S. Cl. .................... 424/452; 514/54; 424/442

(58) Field of Classification Search .............. None
See application file for complete search history.

(56) References Cited

U.S. PATENT DOCUMENTS

| 4,303,676 A | 12/1981 | Balazs |
| 4,808,576 A | 2/1989 | Schultz et al. |
| 5,470,578 A | 11/1995 | Aoki et al. |
| 5,633,003 A | 5/1997 | Cantor |
| 6,159,955 A | 12/2000 | Asculai et al. |
| 6,607,745 B2 * | 8/2003 | Leneau ............ 424/439 |
| 6,924,273 B2 * | 8/2005 | Pierce ............ 514/54 |

FOREIGN PATENT DOCUMENTS

| JP | 9262057 | 10/1997 |
| WO | WO 92/22585 | 12/1992 |
| WO | WO 97/25051 | 7/1997 |
| WO | WO 00/44367 | 8/2000 |

OTHER PUBLICATIONS

"Hyaluronan (Hyaluronic acid, Synvise, Hyalgan)" from website www.midwestarthritis.com/html/hyaluronic_acid.htm.
"Fibromyalgia Basics—Symptoms, Treatments and Research", from website www.fmnetnews.com/pages/basics.html.

* cited by examiner

*Primary Examiner*—M P Woodward
*Assistant Examiner*—Aradhana Sasan
(74) *Attorney, Agent, or Firm*—Ice Miller LLP

(57) ABSTRACT

Methods and compositions are described for relieving joint pain and discomfort in a warm-blooded vertebrate by delivering via oral ingestion a nutritional supplement comprising an effective amount of hyaluronic acid, or a salt or digest thereof, and a nutritionally acceptable carrier.

10 Claims, No Drawings

INGESTION OF HYALURONIC ACID FOR IMPROVED JOINT HEALTH

CROSS-REFERENCE TO RELATED APPLICATION

This application is a continuation-in-part of U.S. patent application Ser. No. 09/860,425, filed May 18, 2001, now U.S. Pat. No. 6,607,745, herein incorporated by reference.

FIELD OF THE INVENTION

The present invention relates to a method for relieving joint pain or other discomfort in a warm-blooded vertebrate. More particularly, this invention provides relief of symptoms of arthritic disorders or fibromyalgia by oral ingestion of a composition comprising an effective amount of hyaluronic acid, or a salt or digest thereof.

BACKGROUND AND SUMMARY OF THE INVENTION

Arthritic disorders, including acute and chronic rheumatoid arthritis and osteoarthritis as well as inflammatory skeletal and musculoskeletal conditions, affect millions of people. It has been estimated that 80% of all individuals over the age of 55 suffer from some form of arthritic disorder. The most common arthritic disorder is osteoarthritis. Osteoarthritis develops gradually over time in many cases. Patients experience alternating periods of mild to moderate pain, stiffness, and swelling of the joint and periods of relatively symptom-free joint activity.

Osteoarthritis is characterized by the deterioration of cartilage that covers the ends of bones at a joint, such as the knee or hip. In the healthy joint, cartilage acts as a shock absorber and aids the joint in bearing the stress of physical movement. In addition, synovial joint fluid produced by the synovial membrane lubricates the joint providing a slippery surface over which the bones may move. But as cartilage deteriorates, the bones begin to rub against each other causing joint pain. At the same time, the concentration of hyaluronic acid in the synovial joint decreases, reducing the lubrication ability of the synovial joint fluid. Also, joint movement may be restricted as bone ends erode or thicken, and the bones may develop painful outgrowths, or bone spurs, as a result of this erosion or thickening. If left untreated, cartilage deterioration can seriously weaken the joint, possibly to the point of deformity.

Current methods of reducing pain in osteoarthritic joints include treatment with analgesics or anti-inflammatory medications, physical therapy, topical application of hyaluronic acid to the joint, and intra-articular injection of hyaluronic acid directly into the joint. The primary goal of treatment is reduction of pain and maintenance of joint function and strength. Intra-articular injections of hyaluronic acid, known as viscosupplementation, have seen wide use for patients who have not responded well to other therapies.

Fibromyalgia is a common disabling disorder characterized by chronic musculoskeletal aches and pain, stiffness, general fatigue, and sleep abnormalities. The disorder affects 2-4% of the population and is most frequently found in women between 20 and 50 years old. The exact cause of fibromyalgia remains uncertain, and diagnosis is difficult due to the general nature of the symptoms. Currently, the most effective treatment for fibromyalgia includes a combination of analgesics, sleep aids, exercise programs, relaxation techniques and other measures to reduce muscle tension. These treatments are geared toward improving sleep quality and reducing pain.

Rheumatoid Arthritis is a chronic, systemic, inflammatory disease that chiefly affects the synovial membranes of multiple joints in the body. Rheumatoid arthritis is considered to be an autoimmune disease, in which the patient has remissions and exacerbations of the symptoms. Joints that are actively involved with the disease are usually tender, swollen, and likely demonstrate reduced motion. Several different classes of drugs are often use to treat patients with rheumatoid arthritis, including analgesics to control pain, corticosteroids, uric acid-lowering drugs, immunosuppressive drugs, nonsteroidal antiinflammatory drugs, and disease-modifying antirheumatic drugs. Many patients with rheumatoid arthritis also note a decrease in their symptoms after application of heat.

The present invention is directed to a method for relieving joint and musculoskeletal discomfort in warm-blooded vertebrates comprising the step of delivering to the vertebrate by oral ingestion a composition comprising an effective amount of hyaluronic acid, or a salt or digest thereof, and an acceptable ingestible carrier. The method is used with advantage in treating conditions associated with arthritis and for reducing the discomfort of fibromyalgia in a person afflicted with fibromyalgia.

Additional features of the present invention will become apparent to those skilled in the art upon consideration of the following detailed description of the preferred embodiments.

DETAILED DESCRIPTION OF THE INVENTION

Hyaluronic acid is a mucopolysaccharide that is found in joint tissue and in the vitreous humor of the eye. Hyaluronic acid functions as a protective coating and a lubricant for soft tissue and joints, and additionally, helps maintain the structural integrity of soft tissue. In association with protein, hyaluronic acid binds water in the intercellular spaces and holds cells together in a jelly like matrix. This jellylike matrix provides lubrication and shock absorption throughout the body.

In the healthy knee joint, hyaluronic acid is present both in the cartilage covering the ends of bone and in the synovial joint fluid. Hyaluronic acid is usually found as part of proteoglycan aggregates in cartilage, where it helps cartilage withstand forces of weight bearing and joint movement. Hyaluronic acid is also a major component of synovial joint fluid. The synovial joint fluid provides lubrication for the cartilage against the lining of the joint and may provide some additional shock-absorption value.

Hyaluronic acid is commercially available and is prepared from the intracellular matrices of animal connective tissue, such as rooster combs and bovine tissue sources, mammalian umbilical cords, and bacterial organisms such as *streptococcus zoepidicus*. Its molecular weight ranges from about 50000 to about $8 \times 10^6$ Daltons depending on source and method of isolation. Treatment with hyaluronidases can be used to provide hydrolysates of reduced molecular weight range.

The present method provides relief from joint pain and musculoskeletal discomfort in a warm-blooded vertebrate suffering from an arthritic condition or fibromyalgia. An arthritic condition includes acute and chronic rheumatoid arthritis and osteoarthritis, as well as inflammatory conditions involving skeletal conditions and musculoskeletal conditions.

In accordance with the present invention, a method is provided for relieving joint or musculoskeletal pain or discomfort in a warm-blooded vertebrate comprising delivering to the vertebrate by oral ingestion a composition comprising an effective amount of hyaluronic acid, or a salt or digest thereof, and a nutritionally acceptable carrier. An "effective amount" as used herein refers to the amount of hyaluronic acid which, upon oral administration, provides relief of joint pain or discomfort. The effective amount of hyaluronic acid, or a salt or digest thereof, is from about 0.1 µg/kg to about 400 µg/kg of body weight per dose. The warm-blooded vertebrate may be a human, or an equine, canine, or feline species. In one embodiment the method is used to reduce joint pain in a person afflicted with osteoarthritis.

In another embodiment the method is used for reducing the discomfort of fibromyalgia. The hyaluronic acid, salt or digest is orally ingested with an acceptable carrier, typically an aqueous beverage or food product. Preferably, the hyaluronic acid, salts, or hydrolysates for use in the present invention are formulated into a liquid aqueous concentration, for example, a dietary supplement formulation, which is diluted in portions and mixed with food, water, or other beverages for oral ingestion. Alternatively the hyaluronic acid, salt, or hydrolysate can be packaged in individual solid or liquid doses, for instance in capsules or gel seals. The concentrate can contain about 1 to about 10 mg of hyaluronic acid, its salt, or hydrolysate per milliliter of concentrate. In one embodiment a dose is administered by combining 7 to 10 drops of the concentrate in a cold beverage which is consumed on conjunction with a meal, for example.

EXAMPLES

Example 1

Oral Ingestion of Hyaluronic Acid by Patients Suffering from Osteoarthritis

A study involving sixty-seven patients suffering from osteoarthritis was undertaken to determine the effectiveness of oral ingestion of hyaluronic acid. Each patient received 1-4 mg of hyaluronic acid by oral ingestion administration 1 to 4 times a day over periods ranging from about 4 to about 2 weeks, during which period the patients' subjective pain feeling was reported. Twenty-nine patients (43.3%) reported no pain after oral ingestion of hyaluronic acid, and additionally reported increased range of motion. Twenty-four patients reported (35.8%) some degree of pain relief and some increased range of motion. Fourteen patients reported no change in the amount of pain they felt.

Example 2

Oral Ingestion of Hyaluronic Acid by Patients Afflicted with Fibromyalgia

Another study involving thirty-five human patients suffering pain and discomfort associated with fibromyalgia was undertaken to evaluate the effectiveness of oral ingestion of hyaluronic acid. Each patient received about 1 to about 6 mg of hyaluronic acid by oral ingestion administration of concentrate diluted into beverages or food. Over a treatment period of about 1 to about 14 months, the patients' subjective pain feeling was reported. Twenty-one patients reported no pain after hyaluronic acid therapy. Six patients (17.1%) reported some (60%) degree of pain relief. Eight patients reported no change in the amount of pain they felt.

Example 3

Oral Ingestion of Hyaluronic Acid by Patients Afflicted with Rheumatoid Arthritis Another study involving seventeen human patients suffering pain and discomfort associated with rheumatoid arthritis was undertaken. Each patient received about 1 mg of an oral hyaluronic acid solution for a period of 30 days. Each patient was asked to evaluate his or her subjective pain feeling and report the score on a scale of 0 to 10, wherein 0 means no pain and/or stiffness whatsoever and 10 means worst imaginable pain and/or stiffness. Prior to the start of the study, the patients reported as follows:

| | |
|---|---|
| 1 patient reported | 7 |
| 8 patients reported | 8 |
| 4 patients reported | 9 |
| 2 patients reported | 10 | for an average of 8.47. At the completion of the 30-day study, the patients responded as follows:

| | |
|---|---|
| 1 patient reported | 0 |
| 1 patient reported | 1 |
| 3 patients reported | 2 |
| 7 patients reported | 3 |
| 2 patients reported | 7 |
| 1 patient reported | 10 | for an average of 3.47, which is considerably lower than the pain reported prior to treatment. Two of the seventeen patients did not respond to the questionnaire.

Given that oral ingestion of hyaluronic acid reduced join pain and other discomforts due to osteoarthritis, fibromyalgia, and rheumatoid arthritis, it is expected that oral ingestion of hyaluronic acid would reduce joint pain and stiffness resulting from a variety of conditions.

Although the invention has been described in detail with reference to certain preferred embodiments, those skilled in the art will recognize that the invention can be practiced with variations and modifications within the scope and spirit of the invention as described and defined in the following claims.

I claim:

1. A method for relieving joint pain or other discomforts associated with joint disorders in a warm-blooded vertebrate consisting of the step of delivering to said vertebrate by oral ingestion a nutritional supplement consisting essentially of an effective amount of hyaluronic acid, or a salt or digest thereof, and a food acceptable carrier, wherein the effective amount of hyaluronic acid, or a salt or digest thereof, is from about 0.1 µg to about 400 µg/kg of body weight.

2. The method of claim 1 wherein the nutritional supplement is provided in capsule form.

3. The method of claim 1 wherein the warm-blooded vertebrate is a human, or an equine, canine, or feline species.

4. The method of claim 1 wherein the joint pain is the result of an arthritic condition.

5. The method of claim 4 wherein the arthritic condition is selected from the group consisting of osteoarthritis and rheumatoid arthritis.

6. The method of claim 1 wherein the joint pain is the result of an inflammatory condition involving skeletal or musculoskeletal structures.

7. A nutritional supplement consisting essentially of an effective amount of hyaluronic acid, or a salt or digest thereof, and a food acceptable carrier, the nutritional supplement provided in an orally ingestible dosage form.

8. The nutritional supplement of claim 7, wherein the effective amount of hyaluronic acid is 1 to 6 mg.

9. The nutritional supplement of claim 7 wherein the orally ingestible dosage form is a capsule or gel seal.

10. The method of claim 1 wherein the effective amount of hyaluronic acid, or a salt or digest thereof, is provided in liquid form.

\* \* \* \* \*